US012721649B1

(12) United States Patent
Wan et al.

(10) Patent No.: US 12,721,649 B1
(45) Date of Patent: Sep. 1, 2026

(54) WIRELESS TRANSMISSION-BASED VISUALIZED PUNCTURE DEVICE AND USE METHOD THEREOF

(71) Applicant: Changzhou Xin Neng Yuan Medical Stapler Co., Ltd., Changzhou (CN)

(72) Inventors: Jianfeng Wan, Changzhou (CN); Yufei Ma, Changzhou (CN)

(73) Assignee: Changzhou Xin Neng Yuan Medical Stapler Co., Ltd., Changzhou (CN)

( * ) Notice: Subject to any disclaimer, the term of this patent is extended or adjusted under 35 U.S.C. 154(b) by 0 days.

(21) Appl. No.: 19/214,072

(22) Filed: May 21, 2025

(30) Foreign Application Priority Data

Apr. 3, 2025 (CN) ........................ 202510419147.2

(51) Int. Cl.
*A61B 17/34* (2006.01)
*A61B 17/00* (2006.01)
*A61B 90/00* (2016.01)

(52) U.S. Cl.
CPC ........ *A61B 17/3421* (2013.01); *A61B 90/361* (2016.02); *A61B 90/37* (2016.02); *A61B 2017/00199* (2013.01); *A61B 2017/00221* (2013.01); *A61B 2017/00862* (2013.01); *A61B 2090/373* (2016.02)

(58) Field of Classification Search
CPC ............. A61B 17/3421; A61B 90/361; A61B 2090/373; A61B 2017/00199; A61B 2017/00221; A61B 2017/00862; A61B 90/37
See application file for complete search history.

(56) References Cited

U.S. PATENT DOCUMENTS 10,827,907 B2 * 11/2020 Kunz ........................ A61B 1/05
10,944,949 B2 * 3/2021 Miyazaki ........... A61B 1/00087
11,534,079 B2 * 12/2022 Page ...................... A61B 5/065
2017/0042573 A1 2/2017 Savvouras et al.
2018/0014759 A1 * 1/2018 Bechtel ................ A61B 5/1459
2018/0014851 A1 * 1/2018 Hansen .............. A61B 17/3421
2019/0110674 A1 * 4/2019 Allen ..................... A61B 1/126
2021/0290311 A1 * 9/2021 Fuerst .................... B25J 19/027

FOREIGN PATENT DOCUMENTS

WO 2020040652 A 2/2020

* cited by examiner

*Primary Examiner* — Eduardo C Robert
*Assistant Examiner* — Holly Joanna Lane
(74) *Attorney, Agent, or Firm* — Vanguard IP LLC; Michael D. Eisenberg

(57) ABSTRACT

The present application pertains to the field of puncture devices, and specifically relates to a wireless transmission-based visualized puncture device. This device integrates wireless transmission technology and visualization display technology to achieve real-time monitoring and remote control during the puncture procedure. Users can view high-definition images of the puncture site in real time through wireless connection and perform precise puncture operations as required. Furthermore, the device has the advantage of easy operation, high safety and reliability, and broad applicability, providing a more efficient and convenient puncture solution for medical, biological research, and related fields.

8 Claims, 8 Drawing Sheets

WIRELESS TRANSMISSION-BASED VISUALIZED PUNCTURE DEVICE AND USE METHOD THEREOF

TECHNICAL FIELD

The present application pertains to the technical field of puncture devices, and particularly relates to a wireless transmission-based visualized puncture device and its method of use.

BACKGROUND

Puncture procedures are important clinical examination and treatment techniques that play a significant role in disease diagnosis and therapy. Commonly used clinical puncture assemblies typically consist of a puncture needle and a puncture cannula. During the procedure, the puncture needle is inserted into the puncture cannula and advanced to the predetermined position, after which the puncture needle is withdrawn and subsequent clinical operations are performed.

In certain abdominal surgeries, it may be necessary to connect an insufflator after puncture to establish an artificial pneumoperitoneum. The mechanical pressurized insufflation provided by the insufflator separates the abdominal wall from the organs, thereby creating sufficient operative space. However, traditional puncture methods do not allow for visualization of the puncture depth, cannot ensure the safety of the puncture procedure, and also do not permit observation of the effectiveness of abdominal insufflation, thereby increasing intraoperative safety risks. If, after withdrawing the puncture needle, an endoscope is inserted into the puncture cannula for observation and manipulation, it is difficult to maintain the stability of the endoscope, which significantly increases the operational difficulty for medical personnel, and it remains challenging to observe the puncture depth in real time.

SUMMARY

To address the aforementioned issues, the present application provides a wireless transmission-based visualized puncture device and a use method thereof.

A wireless transmission-based visualized puncture device, comprising a puncture cannula assembly, an adapter cap assembly, and a puncture needle assembly;

The puncture cannula assembly comprises a cannula base, a puncture cannula is arranged on the cannula base.

The adapter cap assembly comprises an adapter cap, wherein the puncture cannula is connected to the adapter cap via a first buckle, an inflation port is provided on the side wall of the adapter cap, an inflation switch is arranged on one side of the inflation port.

The puncture needle assembly comprises a handle housing, the handle housing is connected to the adapter cap via a second buckle, wherein a puncture needle tube, adapted to the puncture cannula, is arranged below the handle housing, and a first through hole for passing the puncture needle tube is arranged in the middle of the adapter cap.

A camera lens is arranged on the inner side of the lower part of the puncture needle tube, wherein the camera lens is connected to a PCB board, and the PCB board is connected to a wireless signal transceiver.

Furthermore, the PCB board is connected to a gyroscope.

Furthermore, a visualization component mounting tube is arranged on the inner side of the puncture needle tube; the camera lens is arranged on the inner side of the lower part of the visualization component mounting tube; the PCB board is arranged on the inner side of the visualization component mounting tube and is connected to a button switch; a pressing column is arranged above the button switch; the lower part of the pressing column is arranged on the inner side of the visualization component mounting tube; and a first opening is arranged at the upper part of the handle housing to expose the upper part of the pressing column.

Furthermore, block-shaped protrusions are arranged on both sides of the lower part of the pressing column, and limiting grooves adapted to the block-shaped protrusions are arranged on both sides of the upper part of the visualization component mounting tube.

Furthermore, the second buckle comprises an elastic member made of elastic material, the cross-section of the elastic member is semicircular; the central part of the elastic member is provided with a second opening for passing the pressing column, and both sides of the elastic member are connected to sheet-shaped first withdrawal buttons; third openings for exposing the first withdrawal buttons are provided on both side walls of the handle housing.

A first laminar body is arranged below the withdrawal button; a first strip-shaped protrusion is arranged on the outer side of the lower part of the first laminar body; both sides of the upper part of the adapter cap are provided with first insertion slots for accommodating the first laminar body, and the inner wall of each first insertion slot is provided with a slot adapted to the first strip-shaped protrusion.

Furthermore, the adapter cap comprises an adapter cap upper cover and an adapter cap lower cover, wherein the adapter cap upper cover is arranged above the adapter cap lower cover, and an installation chamber is formed between the adapter cap upper cover and the adapter cap lower cover; in the installation chamber, a sealing valve upper fixing ring, a sealing valve, a sealing valve lower fixing ring, an air-blocking valve compression ring, and an air-blocking valve are arranged in sequence from top to bottom.

Furthermore, the lower part of the adapter cap is sleeved over the outer side of the upper part of the puncture cannula, and a sealing ring is arranged at the junction between the adapter cap and the puncture cannula.

A use method for a wireless transmission-based visualized puncture device, comprising:

- S1: inserting a puncture needle of the same specification into a puncture cannula of the same specification; long pressing the button switch to trigger the wireless signal transceiver to send a puncture device activation signal to an external receiving terminal; then, advancing the tip of the puncture needle into a patient's abdominal cavity;
- S2: after the external receiving terminal receives the puncture device activation signal, receiving the internal images of the puncture site captured by the camera lens and displaying them on a visualization interface of the external receiving terminal;
- S3: briefly pressing the button switch to trigger the wireless signal transceiver to send a puncture completion signal to the external receiving terminal, opening the puncture device insufflation valve, fully releasing the abdominal cavity gas, then withdrawing the puncture needle, removing the puncture device cannula, and suturing each puncture site.

The advantageous effects of the present application are as follows:

(1) Through the coordinated operation of the puncture needle assembly, adapter cap assembly, and puncture cannula assembly, real-time video transmission of the puncture procedure is achieved, ensuring the stability of the transmitted images. This enables observation of puncture depth, enhances the safety of the puncture procedure, and allows monitoring of the abdominal insufflation effect, thereby reducing surgical safety risks;

(2) Through the coordinated operation of the wireless signal transceiver and the external receiving terminal, medical personnel can observe the puncture procedure in real time from a location remote from the surgical site, reducing the operational difficulty for medical staff and improving the convenience and safety of the procedure; Meanwhile, the design of the camera lens and the visualization component mounting tube allows the camera lens to be securely fixed within the puncture needle tube, further ensuring the stability of the imaging and providing strong support for the smooth execution of the procedure.

Other features and advantages of the present application will be described in the following specification and will become apparent in part from the specification or through the implementation of the present application. The objectives and other advantages of the present application may be realized and obtained through the structure indicated in the specification and the figures.

BRIEF DESCRIPTION OF THE DRAWINGS

To more clearly illustrate the technical solution in the embodiments of the present application or the prior art, the figures required in the description of the embodiments or the prior art are briefly introduced below. It is evident that the figures described below represent certain embodiments of the present application. For those skilled in the art, other figures may also be derived from these figures without creative effort.

In the figures: 1. Puncture cannula assembly; 101. Cannula base; 102. Puncture cannula; 103. First buckle; 104. Sealing ring; 2. Adapter cap assembly; 201. First through hole; 202. Adapter cap upper cover; 203. Adapter cap lower cover; 204. Inflation port; 205. Inflation switch; 206. Sealing valve upper fixing ring; 207. Sealing valve; 208. Sealing valve lower fixing ring; 209. Air-blocking valve compression ring; 210. Air-blocking valve; 211. First insertion groove; 3. Puncture needle assembly; 301. Handle housing; 302. Puncture needle tube; 303. Second buckle; 304. Visualization component mounting tube; 305. Camera lens; 306. PCB board; 307. Wireless signal transceiver; 308. Button switch; 309. Pressing column; 310. Battery; 311. Data transmission interface; 312. Limiting groove.

DETAILED DESCRIPTION

To further clarify the objectives, technical solution, and advantages of the embodiments of the present application, the technical solution of the embodiments will be described clearly and comprehensively below with reference to the accompanying figures. It is evident that the described embodiments constitute part of the present application, rather than all embodiments. Based on the embodiments of the present application, all other embodiments that can be obtained by those skilled in the art without inventive effort shall fall within the scope of protection of the present application.

Embodiment 1

Figure 1:
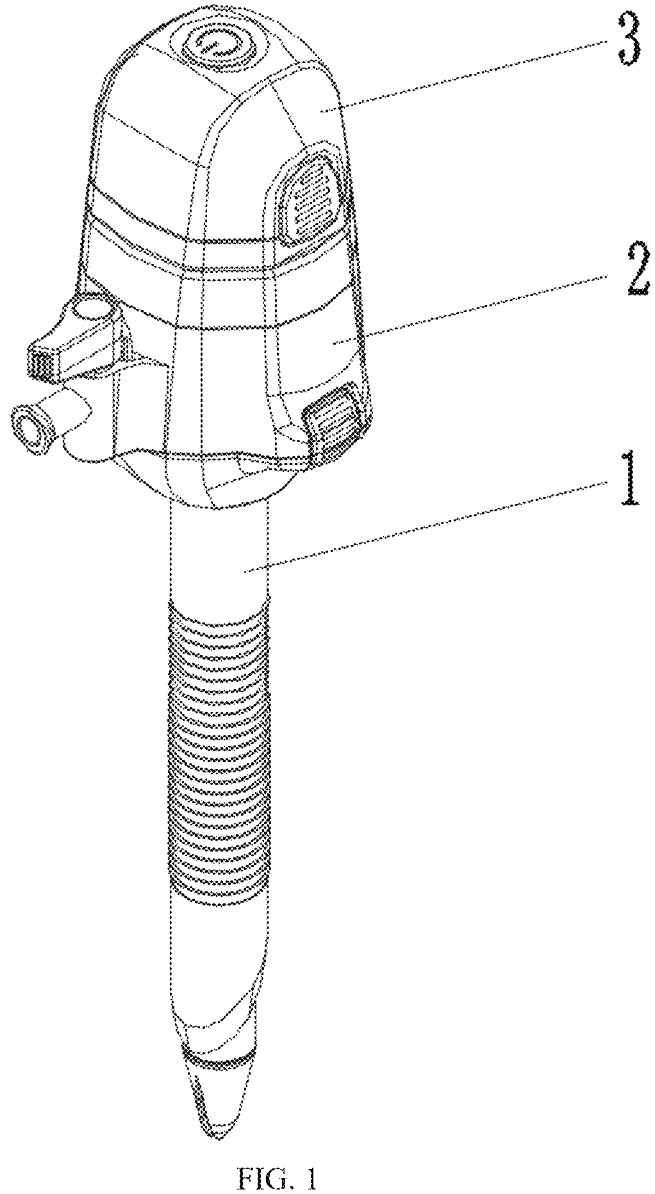
FIG. 1 illustrates a schematic diagram of the present application.
Figure 2:
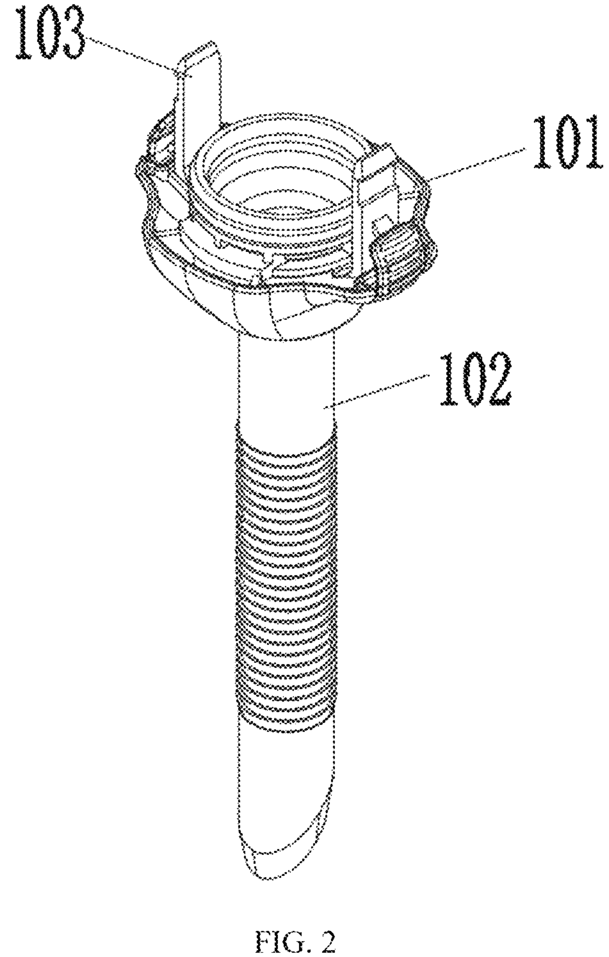
FIG. 2 illustrates a schematic diagram at the puncture cannula assembly of the present application.
Figure 3:
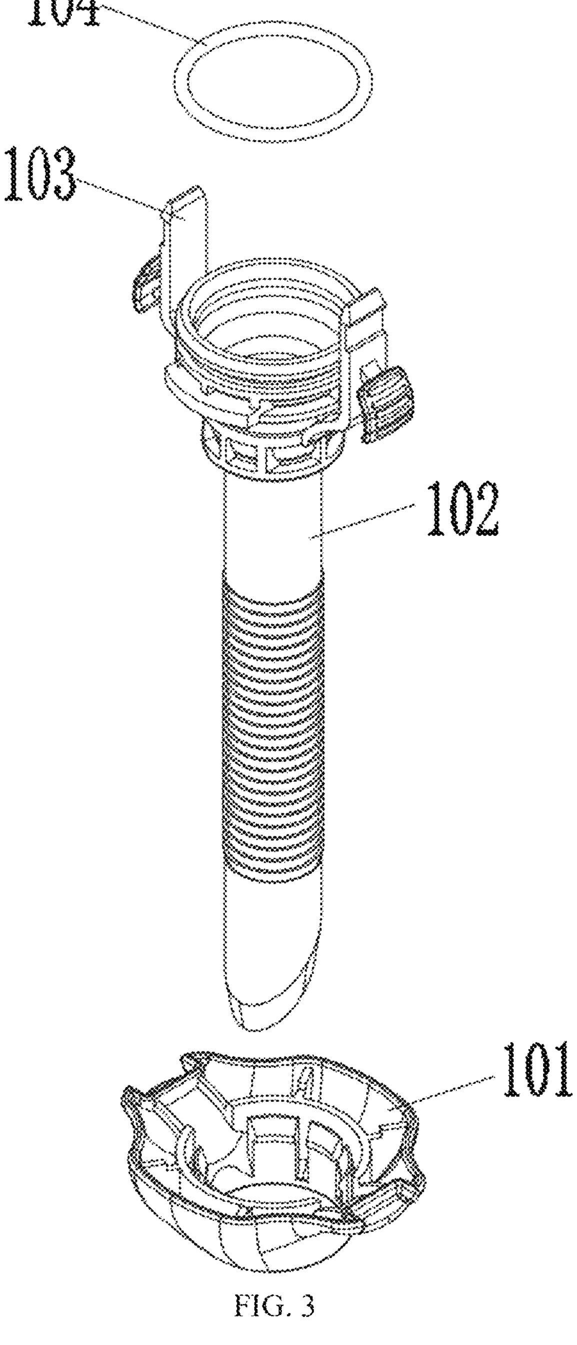
FIG. 3 illustrates an exploded schematic diagram of the puncture cannula assembly of the present application.
Figure 4:
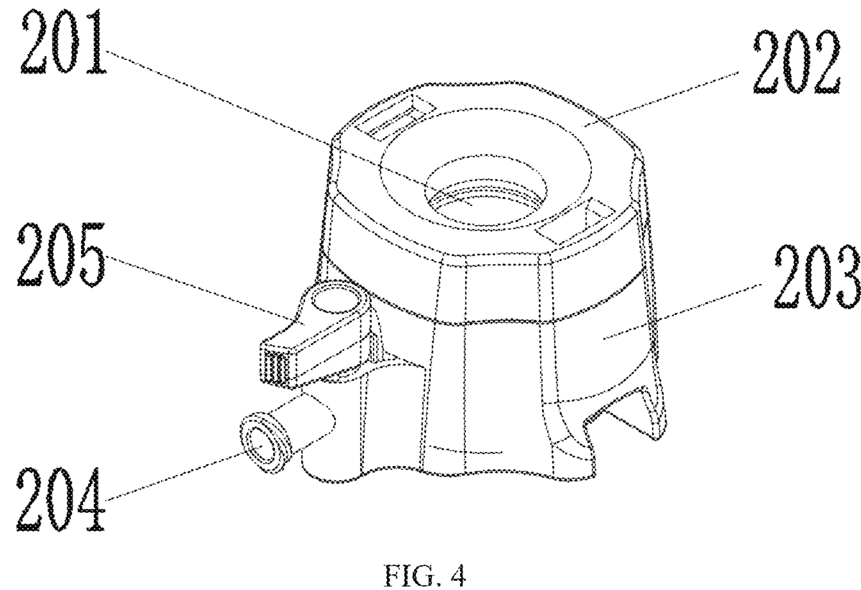
FIG. 4 illustrates a schematic diagram at the adapter cap assembly of the present application.
Figure 5:
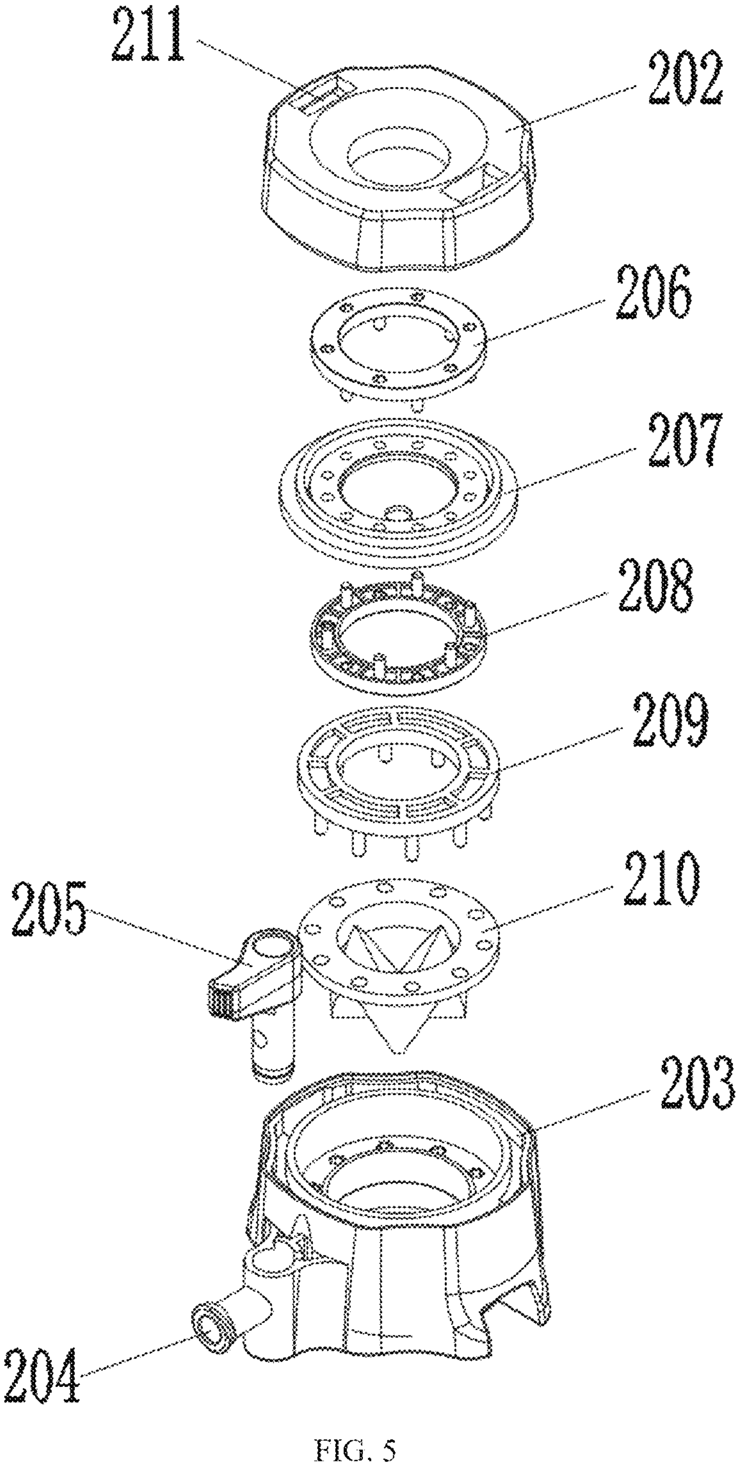
FIG. 5 illustrates an exploded schematic diagram of the adapter cap assembly of the present application.
Figure 6:
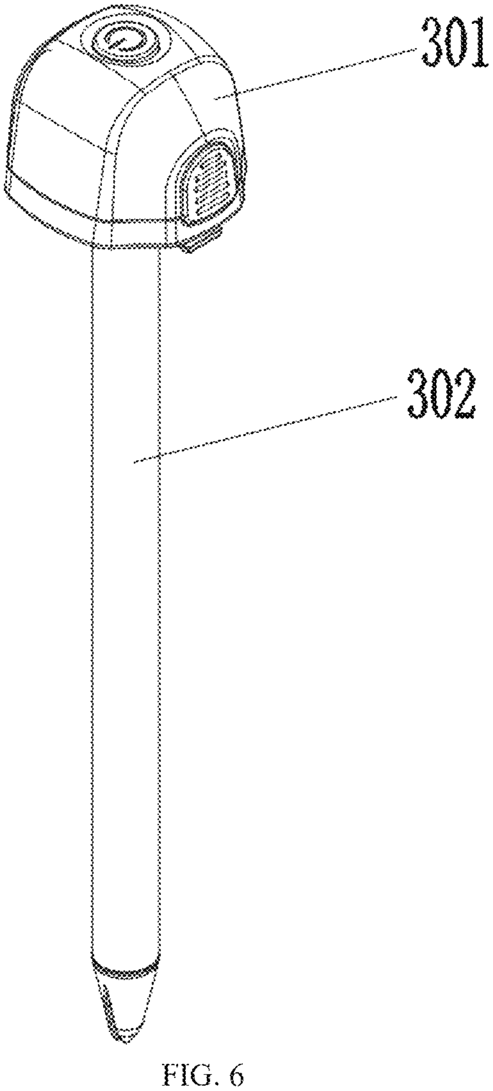
FIG. 6 illustrates a schematic diagram at the puncture needle assembly of the present application.
Figure 7:
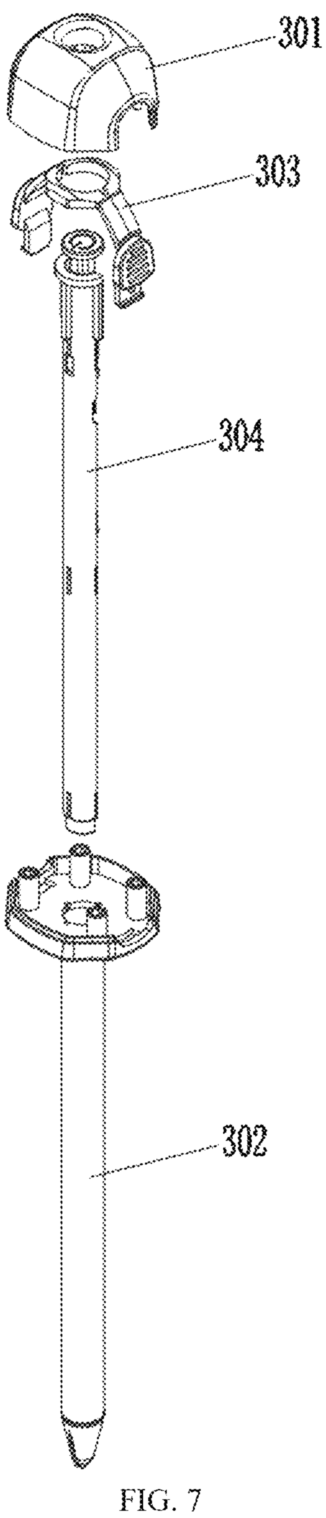
FIG. 7 illustrates an exploded schematic diagram of the puncture needle assembly of the present application.
Figure 8:
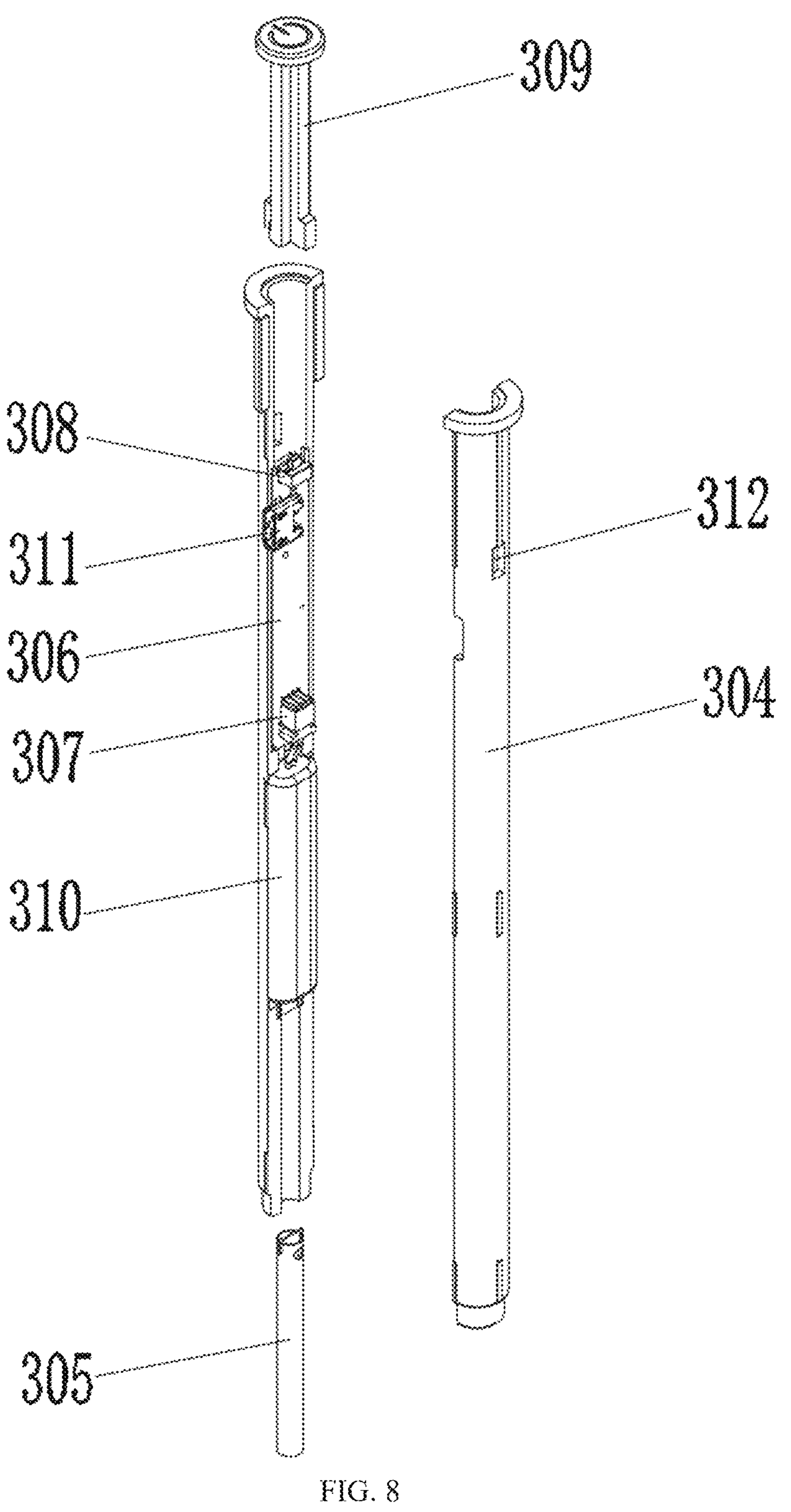
FIG. 8 illustrates an exploded schematic diagram at the visualization component mounting tube of the present application.

As shown in FIGS. 1-8, a wireless transmission-based visualized puncture device comprises a puncture cannula assembly 1, an adapter cap assembly 2, and a puncture needle assembly 3. The puncture cannula assembly 1 comprises a cannula base 101, on which a puncture cannula 102 is arranged. The adapter cap assembly 2 comprises an adapter cap, with the puncture cannula 102 connected to the adapter cap via a first buckle 103. An inflation port 204 is arranged on the side wall of the adapter cap, with an inflation switch 205 arranged on one side of the inflation port 204. The puncture needle assembly 3 comprises a handle housing 301, which is connected to the adapter cap via a second buckle 303. A puncture needle tube 302, adapted to the puncture cannula 102, is arranged below the handle housing 301. A first through hole 201 for passing the puncture needle tube 302 is arranged in the middle of the adapter cap. A camera lens 305 is arranged on the inner side of the lower part of the puncture needle tube 302. The camera lens 305 is connected to a PCB board 306, which in turn is connected to a wireless signal transceiver 307. This design, through the coordinated operation of the puncture needle assembly 3, adapter cap assembly 2, and puncture cannula assembly 1, enables real-time video transmission of the puncture procedure, thereby facilitating the observation of puncture depth and enhancing the safety of the puncture process. Furthermore, in abdominal surgeries requiring the establishment of artificial pneumoperitoneum, the effect of abdominal insufflation can be monitored, thereby reducing safety risks during the procedure.

To ensure the imaging performance of the camera lens 305, both the puncture cannula 102 and the puncture needle tube 302 are made of fully transparent materials.

The PCB board 306 is connected to a gyroscope, which reduces image tilt or shaking caused by operator rotation or accidental contact with the visualized puncture device during the puncture procedure, thereby ensuring the stability of image transmission.

A visualization component mounting tube 304 is arranged on the inner side of the puncture needle tube 302. The camera lens 305 is arranged at the inner side of the lower part of the visualization component mounting tube 304, while the PCB board 306 is arranged on the inner side of the visualization component mounting tube 304. The PCB board 306 is connected to a button switch 308, above which a pressing column 309 is arranged. The lower part of the pressing column 309 is arranged on the inner side of the visualization component mounting tube 304. A first opening is arranged at the upper part of the handle housing 301 to expose the upper part of the pressing column 309. This configuration allows for convenient installation and fixation of the camera lens 305, PCB board 306, button switch 308, and other components via the visualization component mounting tube 304, with the pressing column 309 serving as the power-on key to trigger the button switch 308.

The PCB board 306 is connected to a battery 310, which is arranged inside the visualization component mounting tube 304, thereby supplying electrical power to the PCB board 306 and other components. The battery 310 may be a rechargeable storage battery.

The wireless signal transceiver 307 is arranged on the PCB board 306 and located within the visualization component mounting tube 304. The PCB board 306 is further equipped with a data transmission interface 311 to ensure effective signal transmission, and an opening is provided on the side wall of the visualization component mounting tube 304 to expose the data transmission interface 311. The wireless signal transceiver 307 may be implemented as one of the following modules: Bluetooth, 4G, 5G, or Wi-Fi.

Specifically, the visualization component mounting tube 304 comprises a left mounting semicircular tube and a right mounting semicircular tube adapted to the left. Both the inner walls of the left and right mounting semicircular tubes are provided with a first embedding groove for securing the battery 310. Below the first embedding groove, a second embedding groove is provided for securing the camera lens 305, thereby enhancing the installation stability of components such as the camera lens 305 and the battery 310.

Block-shaped protrusions are arranged on both sides of the lower part of the pressing column 309, while limiting grooves 312, adapted to the block-shaped protrusions, are arranged on both sides of the upper part of the visualization component mounting tube 304. Furthermore, the length of the limiting groove 312 is greater than the thickness of the block-shaped protrusion. Thus, when the block-shaped protrusions on both sides of the lower part of the pressing column 309 are positioned within the limiting groove 312, the vertical movement distance of the pressing column 309 is restricted, thereby ensuring effective triggering of the button switch 308 by the pressing column 309.

The second buckle 303 comprises an elastic member made of elastic material; the cross-section of the elastic member is semicircular. The central part of the elastic member is provided with a second opening for passing the pressing column 309. Both sides of the elastic member are connected to sheet-shaped first withdrawal buttons, and third openings for exposing the first withdrawal buttons are provided on both side walls of the handle housing 301. A first laminar body is arranged below the withdrawal button, a first strip-shaped protrusion is arranged on the outer side of the lower part of the first laminar body. Both sides of the upper part of the adapter cap are provided with first insertion slots 211 for accommodating the first laminar body. The inner wall of each first insertion slot 211 is provided with a first slot adapted to the first strip-shaped protrusion. When the user presses the elastic member inward via the first withdrawal buttons on both sides, the first strip-shaped protrusion disengages from the first slot, allowing the first laminar body to be withdrawn from the first insertion slot 211. This enables the separation of the handle housing 301 from the adapter cap, thereby detaching the puncture needle tube 302 from the puncture cannula 102 and forming an instrument channel, which facilitates other clinical procedures utilizing the puncture cannula 102. Furthermore, to facilitate operation of the first withdrawal button, the outer surface of the first withdrawal button is provided with a first anti-slip pattern.

The adapter cap comprises an adapter cap upper cover 202 and an adapter cap lower cover 203. The adapter cap upper cover 202 is arranged above the adapter cap lower cover 203, and an installation chamber is formed between the adapter cap upper cover 202 and the adapter cap lower cover 203. In the installation chamber, a sealing valve upper fixing ring 206, a sealing valve 207, a sealing valve lower fixing ring 208, an air-blocking valve compression ring 209, and an air-blocking valve 210 are arranged in sequence from top to bottom. The coordinated operation of the sealing valve 207, air-blocking valve 210, and related components provides sealing and air-blocking functions, thereby preventing air leakage and similar issues after withdrawal of the puncture needle tube 302, and thus ensuring the safety of abdominal surgery. To facilitate the secure installation of the sealing valve 207 and the air-blocking valve 210, an inwardly protruding step structure is provided on the inner wall of the first through hole 201. This step structure is annular and located on the inner side of the adapter cap lower cover 203. The sealing valve upper fixing ring 206, sealing valve 207, sealing valve lower fixing ring 208, air-blocking valve compression ring 209, and air-blocking valve 210 are all arranged above the step structure. The lower part of the sealing valve upper fixing ring 206 is equipped with several first fixing posts extending downward. The sealing valve 207 is provided with first insertion holes adapted to the first fixing posts. The upper part of the sealing valve lower fixing ring 208 is equipped with several second fixing posts extending upward, and the sealing valve 207 is provided with second insertion holes adapted to the second fixing posts. The lower part of the air-blocking valve compression ring 209 is equipped with several third fixing posts extending downward. The air-blocking valve 210 is provided with second through holes for passing the third fixing posts, and the stepped structure is furnished with third insertion holes adapted to the third fixing posts.

An installation hole is arranged on the side wall of the adapter cap adjacent to the inflation port 204. The inflation switch 205 comprises a lever and a columnar body, with the lever connected to the upper part of the columnar body. The lower part of the columnar body is inserted into the installation hole and is equipped with a third through hole for communication with the inflation port 204. The inner wall of the installation hole is provided with a fourth through hole adapted to the position of the inflation port 204. The fourth through hole communicates with the first through hole 201, and the third through hole is arranged below the air-blocking valve 210. Upon completion of the laparoscopic procedure, the user may rotate the lever, thereby driving the columnar body to rotate, so that both sides of the third through hole at the lower part of the columnar body are respectively connected to the inflation port 204 and the fourth through hole. Consequently, the sequentially connected inflation port 204, third through hole, fourth through hole, and first through hole 201 form a passage, thereby facilitating the release of abdominal gas. When it is not necessary to release the abdominal cavity gas, simply rotate the lever, which drives the cylindrical body to rotate, thereby disconnecting the third through hole from the inflation port 204 and the fourth through hole. This maintains the sealing and air-blocking state of the puncture cannula 102.

The lower part of the adapter cap is sleeved over the outer side of the upper part of the puncture cannula 102, and a sealing ring 104 is arranged at the connection between the adapter cap and the puncture cannula 102 to ensure effective sealing at the junction. To facilitate installation of the sealing ring 104, the upper part of the puncture cannula 102 is provided with an annular groove for accommodating the sealing ring 104.

The first buckle 103 comprises two second laminar bodies made of elastic material, each arranged on either side of the cannula base 101. The outer side of each second laminar body is connected to a second withdrawal button, and the outer side of the upper part of the second laminar body is provided with a second strip-shaped protrusion. Both lower sides of the adapter cap are equipped with second insertion slots for accommodating the upper parts of the second sheet-shaped bodies. The inner wall of each second insertion slot features a second slot that is compatible with the second strip-shaped protrusion. When the user presses the second withdrawal buttons on both sides of the cannula base 101 inward, the second strip-shaped protrusions disengage from the second slots, allowing the second sheet-shaped bodies to be withdrawn from the second insertion slots. This enables the separation of the cannula base 101 from the adapter cap, thereby facilitating the replacement of the adapter cap and the execution of other clinical procedures. Furthermore, to facilitate pressing the second withdrawal button, a second anti-slip pattern is provided on the outer surface of the second withdrawal button.

Embodiment 2

A use method for a wireless transmission-based visualized puncture device, comprising:

S1: inserting a puncture needle of the same specification into a puncture cannula of the same specification; long pressing the button switch to trigger the wireless signal transceiver to send a puncture device activation signal to an external receiving terminal; then, advancing the tip of the puncture needle into a patient's abdominal cavity;

S2: after the external receiving terminal receives the puncture device activation signal, receiving the internal images of the puncture site captured by the camera lens and displaying them on a visualization interface of the external receiving terminal;

S3: briefly pressing the button switch to trigger the wireless signal transceiver to send a puncture completion signal to the external receiving terminal, opening the puncture device insufflation valve, fully releasing the abdominal cavity gas, then withdrawing the puncture needle, removing the puncture device cannula, and suturing each puncture site.

In this embodiment, the external receiving terminal is a mobile terminal application. The mobile terminal application connects to the puncture device via WIFI, encodes the real-time video stream acquired by the camera, and wirelessly transmits it to the external receiving terminal. The external receiving terminal decodes the received video stream using a decoder, thereby displaying real-time internal images of the puncture site. By observing the visualization interface on the external receiving terminal, the user can clearly view the puncture procedure and the condition inside the abdominal cavity, thereby enabling accurate judgment and operation.

The visualization interface also comprises the functions of screenshot, video recording, and real-time data display to meet the diverse requirements of physicians during surgical procedures. The screenshot function enables the capture of key images, facilitating postoperative analysis and discussion. The video recording function allows for the complete preservation of the entire puncture procedure, providing valuable resources for medical teaching and research.

The specific implementation process is as follows:

High frame rate display is ensured by directly outputting video frames using SurfaceView (Android) or Metal (iOS). The mobile terminal application overlays the puncture path, depth markers, and sensor data (such as pressure or temperature) onto the video image, achieving dynamic rendering through Canvas or Shader.

The mobile terminal application captures a Bitmap (Android) or CVPixelBuffer (iOS) from the current video frame buffer and saves it as a PNG or JPG file. The decoded frames are encoded into MP4 files using MediaMuxer (Android) or AVFoundation (iOS), supporting segmented storage and timestamp marking.

Specifically, synchronization compensation between the video display area of the mobile terminal application and the video stream data acquired by the camera is performed using a temporal dynamic compensation method, which comprises:

S1: for each frame of video acquisition, generating an acquisition timestamp $T_c$ through a high-precision hardware clock; embedding the timestamp and the current device clock $T_d$ during encoding; transmitting the encoded frames and associated sensor data via WIFI, ensuring that each data packet contains the same timestamp;

S2: after establishing the wireless connection, exchanging initial timestamps between the mobile terminal and the camera using an NTP-like mechanism, calculating the clock offset $\Delta = T_m - T_d$; converting the timestamps Tc of subsequent frames to a mobile terminal time: $T_c' = T_c + \Delta$; periodically updating $\Delta$ using $T_d$ in the data packets to compensate for clock drift;

S3: performing dynamic buffer management, storing decoded frames in a priority queue according to the mobile terminal time $T_c'$, and the queue length adapts to network conditions; calculating a data latency $D_t$ for a single frame as $D_t = T_r - T_c'$ on the mobile terminal, where Tr is the timestamp at the receiving end; calculating an average latency $D_a$ and jitter $J = \max(D_1) - \min(D_t)$ of a sliding window based on the data latency $D_t$ for the single frame;

setting the buffer depth according to the calculated average latency and jitter;

increasing the buffer depth, If continuous frame loss occurs in the video stream displayed on the visualization interface;

S4: setting the display time for a prediction frame, where the prediction frame $T_{display} = T_c' + B$, with B representing the buffer depth;

Upon arrival of the VSync signal in the Android/iOS display subsystem (SurfaceView/Metal), selecting the prediction frame $T_{display}$ with a time less than the VSync signal arrival time for the latest frame rendering; if the frame is not ready, repeating the previous frame.

Although the present application has been described in detail with reference to the foregoing embodiments, those of ordinary skill in the art should understand that modifications may still be made to the technical solution described in the above embodiments, or that some technical features therein may be equivalently substituted. Such modifications or substitutions do not depart from the essence of the corresponding technical solution or from the spirit and scope of the technical solutions of the embodiments of the present application.

What is claimed is:

1. A wireless transmission-based visualized puncture device, comprising: a puncture cannula assembly, an adapter cap assembly, and a puncture needle assembly;

wherein the puncture cannula assembly comprises a cannula base, and a puncture cannula is arranged on the cannula base;

wherein the adapter cap assembly comprises an adapter cap, the puncture cannula is connected to the adapter cap via a first buckle, an inflation port is arranged on the side wall of the adapter cap, and an inflation switch is arranged on one side of the inflation port;

wherein the puncture needle assembly comprises a handle housing, the handle housing is connected to the adapter cap via a second buckle, a puncture needle tube adapted to the puncture cannula; is arranged below the handle housing, and a first through hole for passing the puncture needle tube is arranged in the middle of the adapter cap;

wherein a camera lens is arranged on the inner side of the lower part of the puncture needle tube, the camera lens is connected to a PCB board, and the PCB board is connected to a wireless signal transceiver, wherein the second buckle comprises an elastic member made of elastic material, a cross-section of the elastic member is semicircular, a central part of the elastic member is provided with a second opening for passing a pressing column, both sides of the elastic member are connected to sheet-shaped first withdrawal buttons, and third openings for exposing the first withdrawal buttons are provided on both side walls of the handle housing;

wherein a first laminar body is arranged below each of the first withdrawal buttons, a first strip-shaped protrusion is arranged on an outer side of a lower part of the first laminar body, both sides of an upper part of the adapter cap are provided with first insertion slots for accommodating the first laminar body, and an inner wall of each of the first insertion slots is provided with a slot adapted to the first strip-shaped protrusion; and wherein the adapter cap comprises an adapter cap upper cover and an adapter cap lower cover, the adapter cap upper cover is arranged above the adapter cap lower cover, an installation chamber is formed between the adapter cap upper cover and the adapter cap lower cover, and, in the installation chamber, a sealing valve upper fixing ring, a sealing valve, a sealing valve lower fixing ring, an air-blocking valve compression ring, and an air-blocking valve are arranged in sequence from top to bottom.

2. The wireless transmission-based visualized puncture device according to claim 1, wherein the PCB board is connected to a gyroscope.

3. The wireless transmission-based visualized puncture device according to claim 1, wherein a visualization component mounting tube is arranged on the inner side of the puncture needle tube; the camera lens is arranged on a inner side of the lower part of the visualization component mounting tube; the PCB board is arranged on the inner side of the visualization component mounting tube and is connected to a button switch; the pressing column is arranged above the button switch; a lower part of the pressing column is arranged on an inner side of the visualization component mounting tube; and a first opening is arranged at an upper part of the handle housing to expose an upper part of the pressing column.

4. The wireless transmission-based visualized puncture device according to claim 3, wherein block-shaped protrusions are arranged on both sides of a lower part of the pressing column, and limiting grooves adapted to the block-shaped protrusions are arranged on both sides of an upper part of the visualization component mounting tube.

5. The wireless transmission-based visualized puncture device according to claim 1, wherein a lower part of the adapter cap is sleeved over the outer side of the upper part of the puncture cannula, and a sealing ring is arranged at the junction between the adapter cap and the puncture cannula.

6. A use method for the wireless transmission-based visualized puncture device according to claim 3, comprising:

S1: inserting the puncture needle of the wireless transmission-based visualized puncture device into the puncture cannula adapted to the puncture needle tube; long pressing the button switch to trigger the wireless signal transceiver to send a puncture device activation signal to an external receiving terminal; then, advancing the tip of the puncture needle into a patient's abdominal cavity;

S2: after the external receiving terminal receives the puncture device activation signal, receiving the internal images of the puncture site captured by the camera lens and displaying them on a visualization interface of the external receiving terminal;

S3: briefly pressing the button switch to trigger the wireless signal transceiver to send a puncture completion signal to the external receiving terminal, opening the puncture device insufflation valve, fully releasing the abdominal cavity gas, then withdrawing the puncture needle, removing the puncture device cannula, and suturing each puncture site.

7. The use method according to claim 6, wherein the external receiving terminal synchronous compensates a video display area in the visualization interface and video stream data acquired by the camera lens using a temporal dynamic compensation method.

8. The use method according to claim 6, wherein in step S3, the visualization interface further comprises functions of screenshot, video recording and real-time data display.

* * * * *